United States Patent [19]

Mettes et al.

[11] Patent Number: 5,239,856
[45] Date of Patent: Aug. 31, 1993

[54] APPARATUS FOR PRODUCING STANDARD GAS MIXTURES

[75] Inventors: Jacques Mettes, Doylestown, Pa.; Takako Kimura, Toyosato, Japan; Michael Schack, Dusseldorf, Fed. Rep. of Germany

[73] Assignee: L'Air Liquide, Societe Anonyme pour l'Etude et l'Exploitation des Procedes Georges Claude, Paris, France

[21] Appl. No.: 895,835

[22] Filed: Jun. 9, 1992

Related U.S. Application Data

[62] Division of Ser. No. 437,623, Nov. 17, 1989, Pat. No. 5,157,957.

[30] Foreign Application Priority Data

Nov. 21, 1988 [EP] European Pat. Off. ......... 88402919.0

[51] Int. Cl.$^5$ ............................................. G01N 33/00
[52] U.S. Cl. .............................................................. 73/1 G
[58] Field of Search .................. 73/1 G; 436/9, 179; 137/7

[56] References Cited

U.S. PATENT DOCUMENTS

| | | | |
|---|---|---|---|
| 3,298,383 | 1/1967 | Cooper | 137/3 |
| 3,776,023 | 12/1973 | Budd et al. | 73/1 G |
| 3,830,256 | 8/1974 | Cox | 137/606 X |
| 3,875,499 | 4/1975 | Roberts | 73/40.7 X |
| 3,976,450 | 8/1976 | Marcote et al. | 55/269 X |
| 4,094,187 | 6/1978 | Navarre, Jr. | 73/1 G |
| 4,114,419 | 9/1978 | Kimbell | 73/1 G |
| 4,164,862 | 8/1979 | Jackson | 73/25.03 |
| 4,257,439 | 3/1981 | Mayeaux | 137/88 |
| 4,275,752 | 6/1981 | Collier et al. | 137/7 |
| 4,290,296 | 9/1981 | Bredeweg et al. | 73/1 G |
| 4,314,344 | 2/1982 | Johns et al. | 364/500 |
| 4,351,614 | 9/1982 | Garnier | 73/1 G X |
| 4,351,743 | 9/1982 | Hashimoto . | |
| 4,498,496 | 2/1985 | Barcellona et al. | 137/599 |
| 4,565,086 | 1/1986 | Orr, Jr. | 175/40 X |
| 5,054,309 | 10/1981 | Mettes et al. | 137/7 X |

FOREIGN PATENT DOCUMENTS 143738 7/1985 Japan .
2036370 6/1980 United Kingdom ................ 436/179

OTHER PUBLICATIONS

"Minireview Dynamic Gas Mixing Techniques"; *Journal of Biochemical and Biophysical Methods;* 3, No. 4 (Oct. 1980) pp. 233–244; Hans Degn et al.
Patent Abstracts of Japan, vol. 9, No. 314, (P-412) (2037), Dec. 10, 1985, & JP-A-60 143 738, S. Oka, "Manufacture of Diluted Gas".

*Primary Examiner*—Tom Noland
*Attorney, Agent, or Firm*—Oblon, Spivak, McClelland, Maier & Neustadt

[57] ABSTRACT

The present invention provides an apparatus for performing a process for producing standard gas mixtures which entails purifying a raw gas using a gas purifier (3) such as a known two stage gas purifier system, thereby generating a high-purity diluent gas;

mixing the high diluent gas and at least one high-concentration standard gas, by generating a medium-concentration gas mixture; dividing the medium-concentration gas mixture into a first flow and a second flow;

selectively mixing the first flow with a sample gas or a high-purity diluent gas or a mixture thereof, thereby obtaining a standard low-concentration gas mixture; and controlling the pressure of the sample gas, the second flow of the medium-concentration gas mixture and the standard low concentration gas mixture.

12 Claims, 3 Drawing Sheets

APPARATUS FOR PRODUCING STANDARD GAS MIXTURES

This is a division of application Ser. No. 07/437,623, filed on Nov. 17, 1989 and now U.S. Pat. No. 5,157,957.

BACKGROUND OF THE INVENTION

1. Field of the Invention

The present invention relates to manufacture of standard gas mixtures and, more particularly, to a process and an apparatus for producing standard gas mixtures for testing, calibrating, . . . highly sensitive analytical instruments such as an atmospheric-pressure ionization mass spectrometer (APIMS).

2. Description of the Background

A variety of gases are used in manufacturing semiconductor devices such as LSIs. These gases contain impurities. The impurities have an adverse influence on the characteristics of the LSIs. Hence, it is demanded that the gases be as pure as possible. This demand grows stronger, along with the increase in the integration density of LSIs. To meet this demand, a high-accuracy and reliable analysis of gases is required.

The techniques commonly used for analyzing such gases for determining the impurity contents thereof are: gas chromatography, gas chromatography-mass spectroscopy, and Fourier transformed infrared spectroscopy. The detection limit of these techniques are, however, 1 to 10 ppb at best. In view of this, these analytical techniques cannot be said to determine the impurity content of the gases as sensitively as is required for example in the manufacture of LSIs.

Known as apparatus for producing standard gas mixtures for use in the various analytical instruments is a standard gas generator which dilutes a high-concentration gas mixture containing the impurity to be analyzed with a so-called zero gas in one or more stages, thereby generating a standard gas mixture under a predetermined pressure at a predetermined flow rate. This apparatus is very useful in producing standard gas mixture to be used to obtain calibration curves. However, it cannot be employed in the internal standard method or the standard addition method, wherein a known amount of a high-concentration standard gas is added directly to a sample gas. Nor can the apparatus be used to produce a standard gas mixture which contains multiple component gases.

Therefore, it has been demanded that a process and an apparatus be developed which can produce these various gas mixtures.

More generally, most of the following functions are required in the daily practice of gas analysis:
Introduce the gas to be analyzed in a controlled way into the analyzing device;
Add to the gas to be analyzed, calibrated amounts of gaseous species in order to apply the standard addition and internal standard generation methods;
Introduction a blanc or zero gas into the analyzing device;
Add to the zero gas calibrated amounts of gaseous species in order to generate controlled mixtures facilitating the calibration of the analyzing device;
Dilute in a controlled way the gas to be analyzed by the zero gas before introduction of the mixture into the analyzing device. This last point is particularly relevant for very polluted, or toxic and/or corrosive gases. The process and apparatus according to the present invention makes it possible to complete the above functions in a simple and effective way which is specially important when doing ultratrace level analysis.

SUMMARY OF THE INVENTION

The object of the present invention is to provide a process and an apparatus for producing standard gas mixtures, each of which contains different gases and can be used in either the internal standard method or the standard addition method.

According to the present invention, there is provided a process for producing standard gas mixtures, comprising the steps A process for producing standard gas mixtures, comprising the steps of:
Controlling the pressure of a raw gas;
Purifying said raw gas, thereby generating a high-purity diluent gas;
Controlling the flow rate of at least one high concentration standard gas;
Mixing the high-purity diluent gas and said at least one high-concentration standard gas, thereby generating a medium-concentration gas mixture;
Dividing the medium-concentration gas mixture into a first flow and a second flow;
Mixing the first flow with a sample gas or the high purity diluent gas, or a mixture thereof, thereby obtaining a standard low-concentration gas mixture;
Controlling the pressure of the sample gas;
Controlling the pressure of said second flow of said medium concentration gas mixture;
Controlling the pressure of said standard low concentration gas mixture.

Accordingly to this invention, there is provided an apparatus for producing standard gas mixtures comprising:
a plurality of gas sources including a source of raw gas, a source of sample gas and sources of different high-concentration standard gases;
A manifold for gathering the high concentration standard gases from the sources of high concentration standard gases and delivering a high concentration standard gas mixture;
purifying means for purifying the raw gas supplied from said source of raw gas, thereby generating a high purity diluent gas,
dividing means for dividing said high purity diluent gas in a first and second portion;
mixing means for mixing said first portion of said high purity diluent gas with said high concentration standard gas mixture,
dividing means for dividing the medium concentration gas mixture into a first flow and second flow;
means for mixing the second portion of the high purity diluent gas and the sample gas and generating a diluent gas which is either the high purity diluent gas or the sample gas or a mixture thereof;
means for mixing said first flow of said medium concentration gas mixture and said diluent gas generating a standard gas mixture.

The apparatus according to the present invention may further comprise means according to any one of claims 16 to 25.

According to a further embodiment of the invention there is provided an apparatus for producing standard gas mixtures, comprising:

a plurality of gas sources including a source of raw gas and sources of different high-concentration standard gases;

a manifold for gathering the high-concentration standard gases from the sources of high-concentration standard gases and delivering a high-concentration standard gas mixture;

a source of sample gas;

a sample gas passage connected to said source of the sample gas;

means for controlling the pressure of the raw gas;

means for controlling the pressure of the sample gas;

purifying means for purifying the raw gas supplied from said source of raw gas, thereby generating a high purity diluent gas;

means for dividing said high purity diluent gas in a first and second portions, said second portion flowing through first restriction means;

mixing means for mixing the first portion of the high-purity diluent gas with the high-concentration standard gas mixture supplied from said manifold, thereby generating an about homogeneous medium-concentration gas mixture;

means for dividing the medium-concentration gas mixture into a first flow and second flow, said first flow being supplied through second restricting means;

means for controlling the flow rate of the second portion of the high purity diluent gas, said means having a closed position wherein no gas flows, and an open position wherein the flow rate of said diluent gas can be controlled;

means for controlling the flow rate of the sample gas, said means having a closed position wherein no sample gas flows, and an open position wherein the flow rate of the sample gas can be controlled. Third restriction means receiving the second portion of the high purity diluent gas and/or the sample gas and generating a diluent gas;

means for mixing said first flow of said medium-concentration gas mixture and said diluent gas for generating a standard low-concentration gas mixture;

means for controlling the pressure of the second flow of said medium-concentration gas mixture;

means for controlling the pressure of said standard low-concentration gas mixture.

In the present invention, the ratio of one flow of the low-concentration gas mixture to another flow of diluent gas and/or of sample gas, can be set at any desired value.

In the process and the apparatus according to the present invention, a single unit may comprise multiple gas sources including a source of raw gas, a source of a sample gas, and sources of different high-concentration gases. The high-concentration standard gas supplied from any high-concentration standard gas source can be diluted twice, first with a diluent gas obtained by purifying the raw gas supplied from the raw gas source, and then with the diluent gas and/or the sample gas supplied from the sample gas source. Therefore, when the valves coupled to the lines connecting these gas sources are operated, various standard gas mixtures can be produced.

When the line for supplying the sample gas, for example, is closed, the high-concentration standard gas mixture is diluted with the zero gas only, thereby preparing a standard gas mixture. When the branched line of the zero gas for the second dilution is closed, the high-concentration standard gas mixture is diluted, first with the zero gas and then with the sample gas, thereby producing a standard gas mixture. Hence, the process and the apparatus according to the present invention can produce standard gas mixtures which can be utilized in the internal standard method and the standard addition method, thus making calibration curves which can be used in analyzing the sample gas.

Moreover, two or more sources of high-concentration gas mixtures, which are used in the present invention, can be selected by operating the valves coupled to these sources. When various kinds of high-concentration standard gas mixtures are supplied from these sources, the concentrations of the various gases forming the standard gas mixture, i.e., the final product, can be changed independently of one another. In order words, the process and the method according to the present invention can produce a variety of standard gas mixtures which are useful particularly in determing the influence imposed on the analytical results of one gas component from other components.

The basic concept of the present invention is to provide a process and related apparatus wherein, as soon as the high purity diluent gas is generated, no further contaminants such as particles and/or gaseous impurities, . . . are added during the further mixing and/or diluting steps of the process. That means that all the devices used for carrying out those steps are able to generate no additional contaminants. Those devices are generally selected among pipes, such as electropolished pipes, and restriction means, such as needle valves (controllable flowrate), calibrated orifices, small diameter pipes, with appropriate diameters as well as appropriate ratios of diameters when different flow-rates and pressures have to be handled in different lines, the selection of the appropriate ratio of diameters being well-known by the man skilled in the art.

No devices which might potentially be contaminant sources are used in the zero gas lines or the mixing lines in the process or apparatus according to the present invention. Orifices or needle valves, which are not contaminant sources, are generally used in the zero gas lines or mixing lines. In the conventional prior art process and apparatus, mass flow controllers and pressure regulators are placed in the zero gas lines and the mixing lines in order to control the flow rates and pressures of the low-concentration gas mixture. According to the present invention, mass flow controllers and pressure regulators are placed upstream of the gas-purifying means, in the high-concentration standard gas lines, the contamination of which is not so problematical, and in the gas-venting lines which are downstream the gas lines of the system according to the invention which are thus prevent from contamination. This specific arrangement of the mass flow controllers and the pressure regulators is based on the inventors' finding that the controllers and regulators can control correctly the flow rate and pressure of the low-concentration gas mixture.

In the body of the present specification, various steps are defined which may have the following meanings according to the invention:

Controlling the pressure of the raw gas is preferably carried out either before the purification step, by means of a pressure regulator or after the purification step, by means of a back pressure regulator.

Controlling the flow rate of a high concentration standard gas may be preferably accurately carried out either by means of a mass flow controller or a neddle valve associated to a pressure regulator.

Controlling the pressure of the low concentration gas mixture, i.e. the mixture adapted to flow in the analyzer, such as APIMS, is carried out preferably:

- with a back pressure regulator connected at the end of the pipe delivering the low concentration gas mixture, thus avoiding about any contamination of the pipe.
- with the analysis apparatus itself which is sometimes able to control itself said pressure (e.g. when the analysis is carried out at atmospheric pressure).
- with a pressure regulator connected at the output of the analysis apparatus, thus providing no contamination of the low concentration gas mixture.

In the present specification the terms high purity diluent gas or zero gas are equivalent. Such high purity gas is obtained by well-known techniques such as catylisis, chemical conversiom, gettering, ambient temperature physical absorption, cryogenic absorption, filtering with molecular sieves, . . . or a combinaison of those methods, in order to remove about any impurities such as particles and gaseous impurities, . . .

Various appropriate methods are disclosed for example in the article of F. W. Giaccobbe and G. S. Khan, both of American Air Liquide Inc., entitled "Production of ultra high purity nitrogen"—Solid state Technology—July 1987—.

BRIEF DESCRIPTION OF THE DRAWING FIGURES

A variety of embodiments of the present invention will now be described, with reference to the accompanying drawings.

This invention can be more fully understood from the following detailed description when taken in conjunction with the accompanying drawings, in which.

DETAILED DESCRIPTION OF THE PREFERRED EMBODIMENTS

Figure 1:
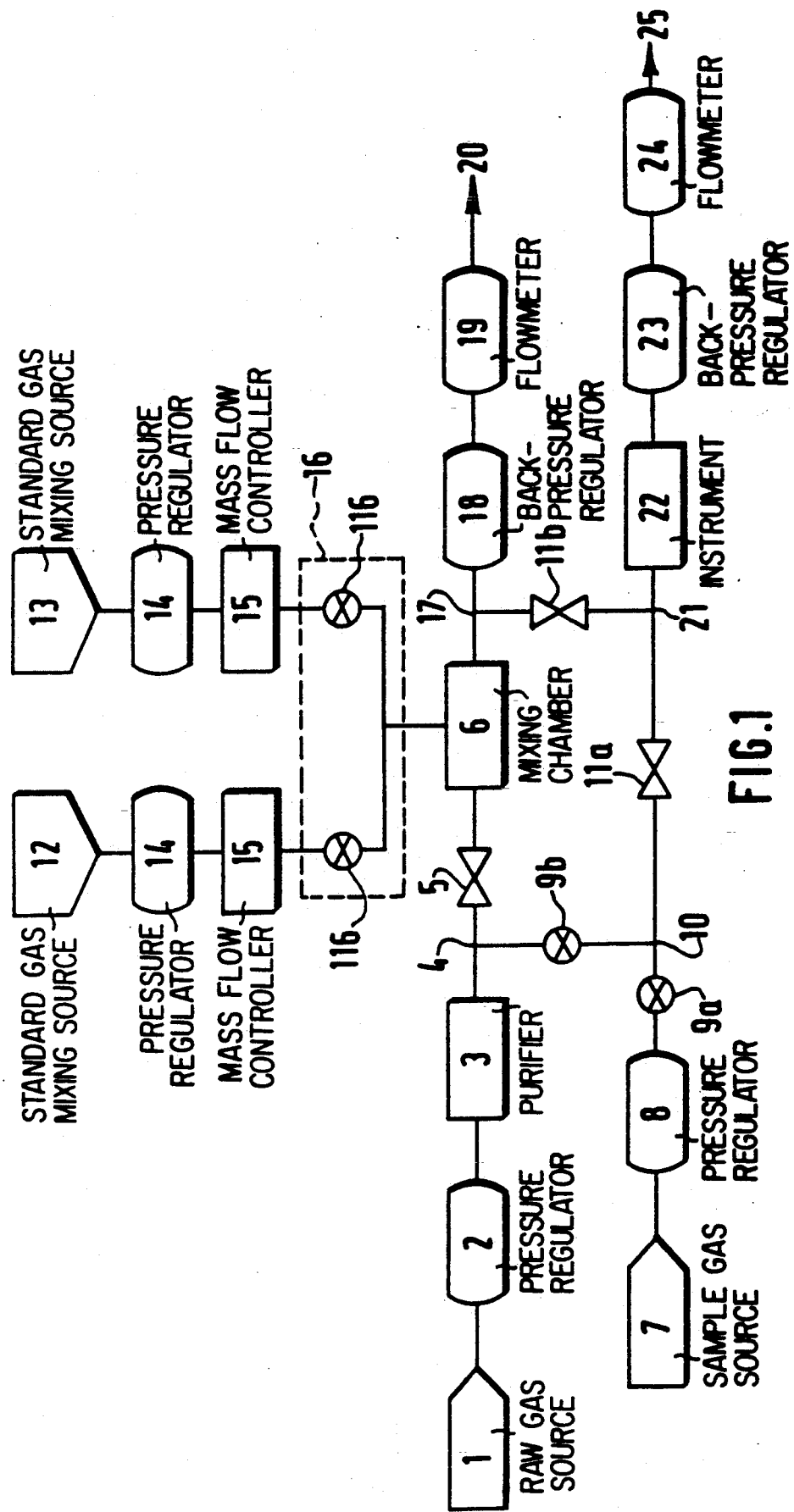
FIG. 1 is a flow diagram explaining how an apparatus according to the invention produces standard gas mixtures.

FIG. 1 is a flow diagram illustrating how an apparatus according to the invention operates to produce standard gas mixtures. As is shown on this FIG. 1, raw gas source 1 is connected to pressure regulator 2, which in turn is coupled to purifier 3. The outlet port of purifier 3 is coupled to branching tube 4 which has two outlets ports. The first outlet port of tube 4 is connected to a needle valve 5. The needle valve 5 is connected to a mixing chamber 6. The second outlet port of tube 4 is coupled to a stop valve 9b, which in turn is connected to one of the two inlet ports of branching tube 10. Sample gas source 7 is connected to a pressure regulator 8. The pressure regulator 8 is coupled to a stop valve 9a. The stop valve 9a is connected to the other inlet port of the branching tube 10. The outlet port of this tube 10 is coupled to a needle valve 11a. A plurality of high-concentration standard gas mixture sources 12 and 13 are connected respectively to a pressure regulator 14. These regulators 14 are coupled respectively to mass flow controllers 15, and mass flow controllers 15 are connected to a manifold 16 which can be an integrated valve (a double 3 ways valve as detailed for example in reference "Nikkei Microdevice, July 1987, challenge to ppt, T. Ohmi"). The outlet port of the manifold 16 is connected to the mixing chamber 6.

The outlet port of the mixing chamber 6 is coupled to the branching tube 17 having two outlets ports. The first outlet port of tube 17 is connected to back-pressure regulator 18, which in turn is coupled to flowmeter 19, which in turn is connected to a gas-discarding port. 20. The second outlet port of the branching tube 17 is coupled to a needle valve 11b. The valve 11b is connected to a branching tube 21 which connects the outlet of the needle valve 11a to an analytical instrument 22. The outlet port of the instrument 22 is coupled to a back-pressure regulator 23, which in turn is connected to a flowmeter 24, which in turn is connected to a gas-discarding port 25.

When the valves coupled to the lines connecting the gas sources of the apparatus described above are operated selectively, various standard gas mixtures can be produced. It will be explained hereafter how this apparatus can realize the various functions referred to hereabove.

The raw gas is supplied from material gas source 1 to the purifier 3 through the pressure regulator 2. Purifier 3, (such as two stages purifier system FP-S and FP-W, sold by Kinki Reinetsu K. K.) purifies the raw gas, thus forming a so called zero gas. Meanwhile, the sample gas is supplied from the gas source 7 to the pressure regulator 8.

The various functions disclosed hereabove and which are required in the daily practice of gas analysis will now be disclosed in more details:

Function 1: Introduce the gas to be analyzed in a controlled way into the analyzing device:

When the valve 9b and the restriction 11b are closed while the valve 9a and the restriction 11a are opened, the sample gas is directly introduced in the analyser, realizing thus mentioned function 1.

Function 2: Add to the gas to be analyzed, calibrated amounts of gaseous species in order to apply the standard addition and internal standard generation methods:

When the valve 9b is closed, and the stop valve 9a and the needle valve 11a are opened, the high-concentration standard gas mixture is diluted first with the zero gas and then with the sample gas, generating a standard gas mixture which is suitable to draw calibration curves for use in both the internal standard method and the standard addition method, thus accomplishing function 2.

Function 3: Introduce a blanc or zero gas into the analyzing device.

When the valve 9a and the supply of high concentration gas mixture from manifold 16 is cut off there are three possible ways of implementing function 3, i.e. the introduction of zero gas (or blanc) into the analyzer:

Closing 9b and opening 5 and 11b,

Closing 5 and 11b while opening 9b and 11a,

Opening 5, 9b, 11a, 11b.

Function 4: Add to the zero gas calibrated amounts of gaseous species in order to generate controlled mixtures facilititating the calibration of the analyzing device;

This function can be carried out for example in one step or two steps:

a—One Step:

When the stop valves 9a and 9b and the needle valve 11a are closed, whereas needle valve 5 is opened, the zero gas is supplied from the purifier 3 to the mixing chamber 6 through the needle valve 5. The zero gas is, therefore, mixed with the high-concentration standard gas mixtures supplied from the plurating of sources 12, . . . 13 through the mixing chamber 6, thus generating a standard gas mixture. The standard gas mixture is divided into two streams by the branching tube 17. The first stream, flows through the back-pressure regulator 18 and the flowmeter 19 and is finally discarded via the gas discarding port 20. The second stream of the standard gas mixture is introduced into the analytical instrument 22 via the needle valve 11b and the branching tube 21. This standard gas mixture has been prepared by diluting the high-concentration gas mixture only one time with the zero gas. It is called a one step dilution gas mixture. This method is, on the other hand, another way to carry out function 4, when the stop valve 9a is closed, b—Two Steps The needle valve 5, the stop valve 9b, and the needle valves 11a and 11b are opened, and the stop valve 9a is still closed. The zero gas from the purifier 3 is divided into two streams by the branching tube 4. As a result, the high-concentration standard gas mixture from the manifold 16 is diluted twice with the zero gas: a first time in the mixing chamber 6 and a second time in the branching tube 21, thus producing a standard low-concentration gas mixture. This constitutes the second way, in two steps to carry out the function 4 of introduction of calibrated mixtures. The possibility to carry out function 4 by the one-step dilution method as well as by the two-step dilution method permits to determine the ratio of the flows involved in the second step of the two-step dilution. With an analyzer and by production of the same amplitude of signal for a certain component added in the one-step or the two-steps methods, it is possible to determine the ratio of the flows added in the second dilution step. The ratio between the flows through the mass flow controller 15 for those two set-ups (one step and two steps dilution) is the ratio of dilution in the second step.

Function 5: Dilute in a controlled way the gas to be analyzed by the zero gas before introduction of the mixture into the analyzing device. This last point is particullarily relevant for very polluted, or toxic and or corrosive gases.

Closing 9b and opening 5, 11b, 11a and 9a allows to dilute the sample gas with the zero gas, thus realizing function 5.

In the present embodiment, either the high-concentration standard gas mixture supplied from one source only or those from a plurality of sources such as 12, . . . 13, can be used to produce multiple standard gas mixtures.

Figure 2:
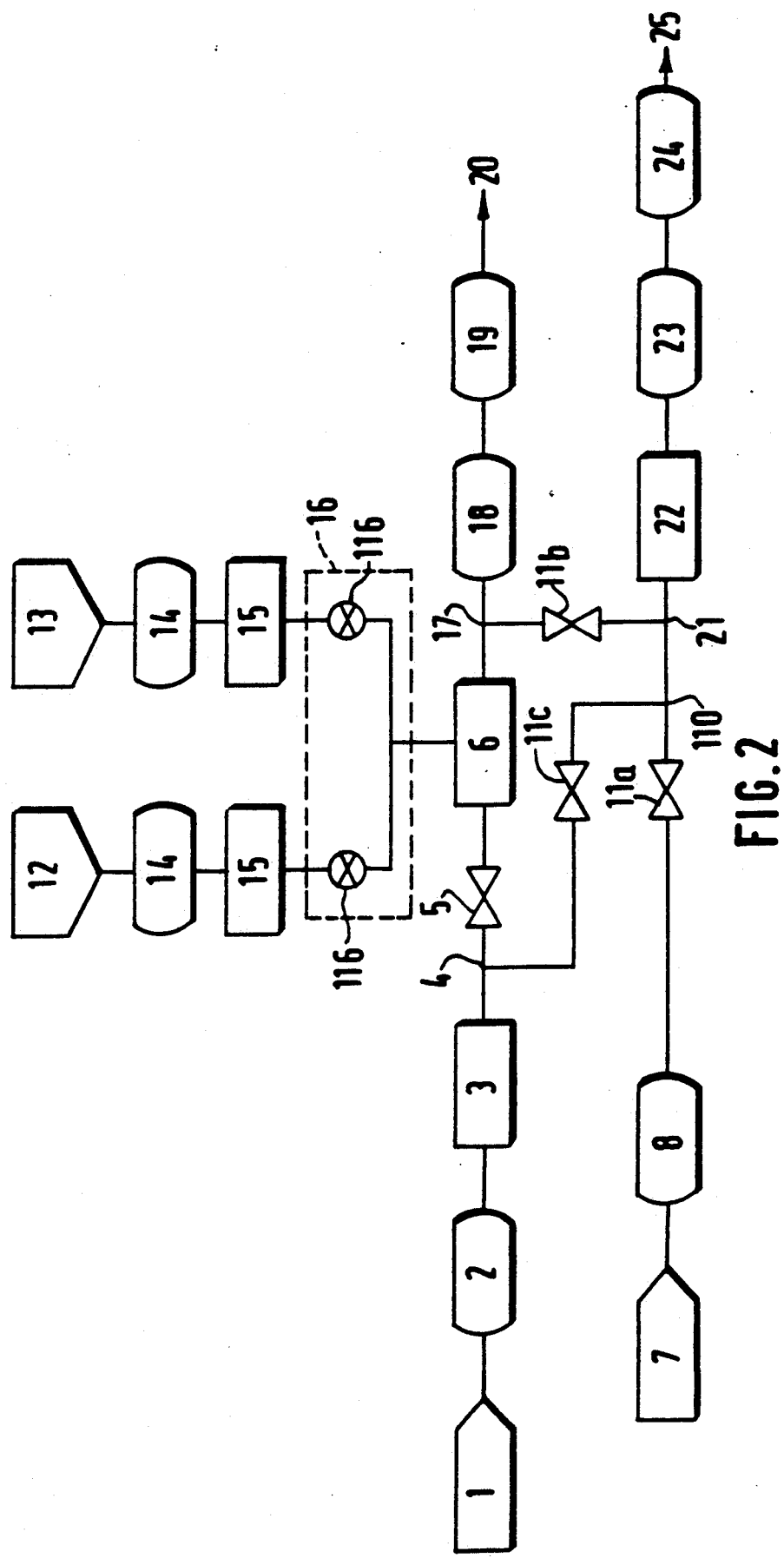
FIGS. 2 and 3 are two other embodiments of the invention.

FIG. 2 is a second embodiment of the invention, the same device as those of FIG. 1 bearing the same references. Valves 9a and 9b are replaced by restrictions 11a and 11c respectively, to control the pressure and the flowrate of the sample gas in combination with pressure regulators 8 and 23 as explained before and of the second portion of the high high purity diluent gas. Thus a ratio of flowrates of each of these gases is fixed and cannot be modified without changing the characteristics of the restrictions. A mixture of those two gases is then made at the T-jonction 110, said mixture being diluted (or mixed) with the first flow of the medium concentration gas mixture coming from the needle valve 11b.

Figure 3:
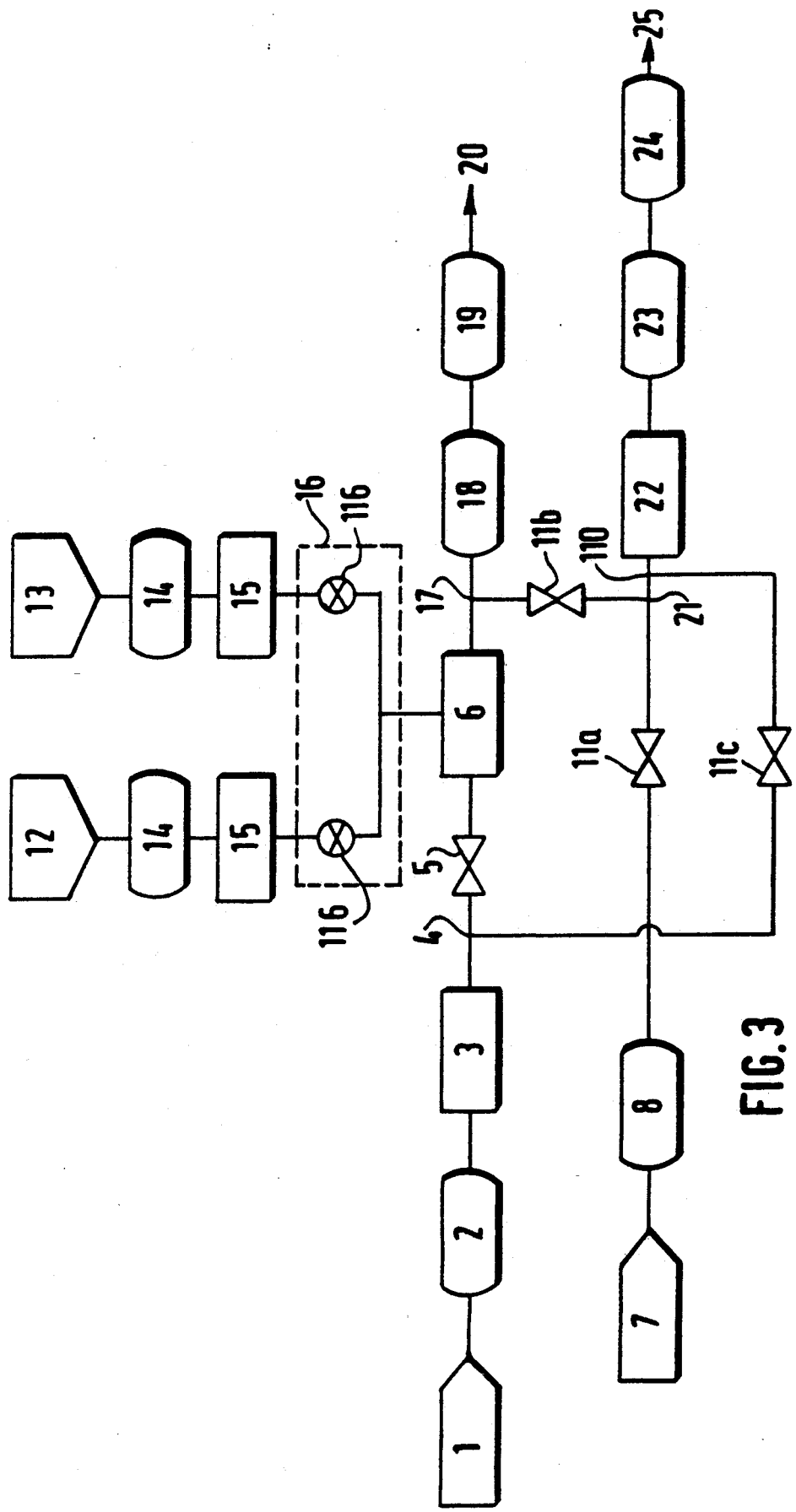

FIG. 3 is another embodiment of the invention where the second portion of the high purity diluent gas is added through needle valve 11c to the mixture flowing from the outlet of the branching tube 21, but before introduction of the same in the analyzer 22.

As described hereabove it is possible according to the present invention to produce a variety of standard gas mixtures by operating the valves coupled to the lines for supplying the zero gas, the sample gas, the high-concentration standard mixture gases, and their mixtures thereof. The standard gas mixtures, thus produced, are suitable to draw calibration curves for use in the internal standard method and the standard addition method.

The apparatus according to the invention has multiple sources of high-concentration standard gas mixtures. Therefore, any possible combination of these gas mixtures can be used, merely by operating valves connected to the outlet ports of these gas mixture sources.

We claim:

1. An apparatus for producing standard gas mixtures, comprising:
    a) a plurality of gas sources including a source of raw gas, a source of sample gas and sources of different high-concentration standard gases;
    b) a manifold for gathering the high concentration standard gases from the sources of high concentration standard gases and delivering a high concentration standard gas mixture;
    c) purifying means for purifying the raw gas supplied from said source of raw gas, thereby generating a high purity diluent gas;
    d) dividing means for dividing said high purity diluent gas into first and second portions;
    e) mixing means for mixing said first portion of said high purity diluent gas with said high concentration standard gas mixture;
    f) dividing means for dividing the medium concentration gas mixture into a first flow and second flow;
    g) means for mixing the second portion of the high purity diluent gas and the sample gas and generating a diluent gas or a mixture thereof; and
    h) means for mixing said first flow of said medium concentration gas mixture and said diluent gas generating a standard gas mixture.

2. The apparatus according to claim 1, further comprising restriction means (5, 11a, 11b, 11c). such that it is selectively either the high purity diluent gas, the sample gas, 3. The apparatus according to claim 1, further comprising means for controlling the pressure of the raw gas.

4. The apparatus according to claim 1, further comprising means for controlling the pressure of the sample gas.

5. The apparatus according to claim 1, further comprising means for controlling the pressure of the second flow of said medium concentration gas mixture.

6. The apparatus according to claim 1, further comprising means for controlling the pressure of said standard low concentration gas mixture.

7. The apparatus according to claim 1, further comprising means for controlling or cutting off the flowrate of the sample gas.

8. The apparatus according to claim 1, further comprising mans for controlling or cutting off the flowrate of the second portion of the high purity diluent gas.

9. An apparatus for producing standard gas mixtures, comprising:

a) a plurality of gas sources, comprising a source of raw gas and sources of different high-concentration standard gases;
b) a manifold for gathering the high-concentration standard gases from the sources of high-concentration standard gases and delivering a high-concentration standard gas mixture;
c) a source of sample gas;
d) a sample gas passage connected to said source of the sample gas;
e) means for controlling the pressure of the raw gas;
f) means for controlling the pressure of the sample gas;
g) purifying means for purifying the raw gas supplied from the source of raw gas, thereby generating a high purity diluent gas;
h) means for dividing said-high purity diluent gas into first and second portions, said second portion flowing through first restricting means;
i) mixing means for mixing the first portion of the high-purity diluent gas with the high-concentration standard gas mixture supplied from said manifold, to generate a substantially homogeneous medium-concentration gas mixture;
j) means for dividing the medium-concentration gas mixture into a first flow and a second flow, said first flow being supplied through second restricting means;
k) means for controlling the flow rate of the second portion of the high purity diluent gas;
l) means for controlling the flow rate of the sample gas;
m) a third restricting means for selectively receiving the second portion of the high purity diluent gas, the sample gas, or both and generating a diluent gas;
n) means for mixing the first flow of said medium-concentration gas mixture and the diluent gas for generating gas for generating standard low-concentration gas mixture;
o) means for controlling the pressure of the second flow of said-medium concentration gas mixtures; and
p) means for controlling the pressure of said low-concentration gas mixture.

10. The apparatus for producing standard gas mixtures according to claim 1 or 9 further comprising means (11c) to cut off the supply of the high concentration gas mixture.

11. The apparatus according to claim 9, wherein the restriction means is selected among calibrated orifice or needle valve.

12. The apparatus according to claim 9 further comprising means for venting said second flow of the medium concentration gas mixture.

* * * * *